United States Patent [19]
Yamamoto et al.

[11] 4,090,401
[45] May 23, 1978

[54] METHOD OF ENDURANCE TEST WITH INITIAL OVERLOADING

[75] Inventors: Shigeru Yamamoto; Takashi Miwa, both of Nagasaki, Japan

[73] Assignee: Mitsubishi Jukogyo Kabushiki Kaisha, Tokyo, Japan

[21] Appl. No.: 798,032

[22] Filed: May 18, 1977

[30] Foreign Application Priority Data

May 18, 1976  Japan .................................. 51-57146

[51] Int. Cl.² ........................................... G01M 15/00
[52] U.S. Cl. .......................................... 73/91; 73/116
[58] Field of Search ............................ 73/116, 100, 91

[56] References Cited
U.S. PATENT DOCUMENTS

3,214,969  11/1965  Swanson .................................. 73/91

FOREIGN PATENT DOCUMENTS

942,526  2/1974  Canada .................................... 73/91

*Primary Examiner*—Jerry W. Myracle
*Attorney, Agent, or Firm*—Wenderoth, Lind & Ponack

[57] ABSTRACT

The known method of endurance test in which a test load is repeatedly applied to a test member, is improved in that in the first test loading cycle an overload is intentionally applied to the test member, but in the second and subsequent test loading cycles a load smaller than that applied in the first cycle is applied to the test member. Owing to such improvement, an endurance test can be accomplished within a shorter period of time without being accompanied by any danger.

1 Claim, 6 Drawing Figures

METHOD OF ENDURANCE TEST WITH INITIAL OVERLOADING

The present invention relates to a method of endurance test in which a load is repeatedly applied to a test member in machines, structures or the like.

Figure 1:
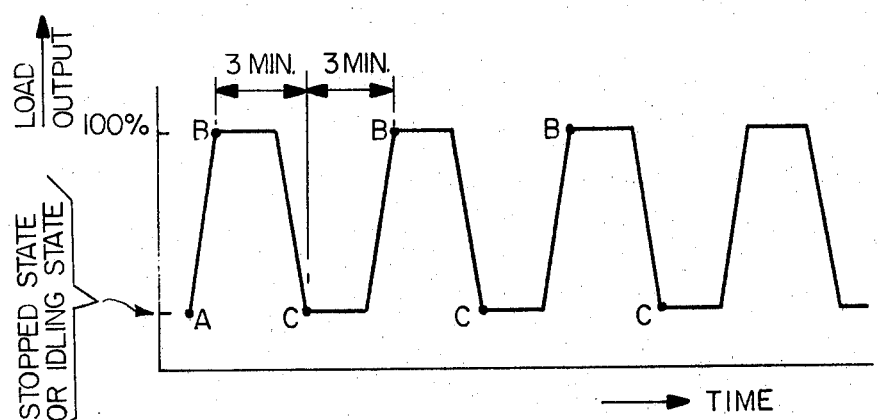

According to the heretofore known endurance test methods, for instance, in case where a test is conducted for a cylinder head in a small-sized internal combustion engine, test cycles of maximum loading—stopping or maximum loading—idling as shown in FIG. 1 were effected until any crack arises in the cylinder head, and thus it was investigated whether or not the number of cycles at which the crack has arisen exceeds a designed goal endurance or a goal endurance determined by empirical results of the products sold in the markets.

Such endurance tests in the prior art required a period of 2 - 3 months and enormous personnel expenses, and especially, upon change of design or development of a new type engine a lot of precious time was spent for such endurance tests and sometimes it was even caused thereby that proper timing for development was lost.

Therefore, in order to shorten the endurance test period varios trials have been made and, for instance, a method of endurance test in which a load is raised higher than 100% and a method in which the test cycles as shown in FIG. 1 are effected under a higher thermal stress than a practical engine by varying a temperature of coolant water for a cylinder head, have been proposed. However, the former method results in unreasonable operations because frequent and excessive variations of output are effected and thus involves a risk of serious accidents and a possibility of destroying component elements other than the cylinder head, while the latter method is limited in the amount of variation of the thermal stress when it is increased larger than that in a practical engine, and has a more fatal disadvantage that the proposed test cannot be an accurate endurance test because it is conducted under an abnormal condition different from operations of a practical engine.

The present invention has been proposed in order to resolve the above-mentioned various problems in the heretofore known method of endurance test, and it is an object of the invention to provide a method of endurance test which is quantitatively correlated with operating conditions of a practical engine and which can be accomplished within a short period without accompanied by danger.

In order to achieve the above object, the method of endurance test according to the present invention is characterized by the feature that in a method of endurance test in which a load is repeatedly applied to a test member, upon first one of said repeated loadings an overload is applied but upon second and subsequent loadings a load smaller than the first load is applied.

Figure 2:
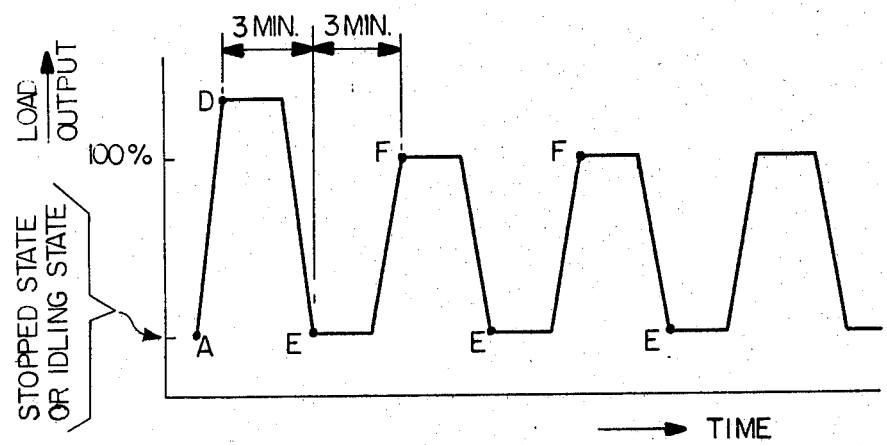
Figure 3:
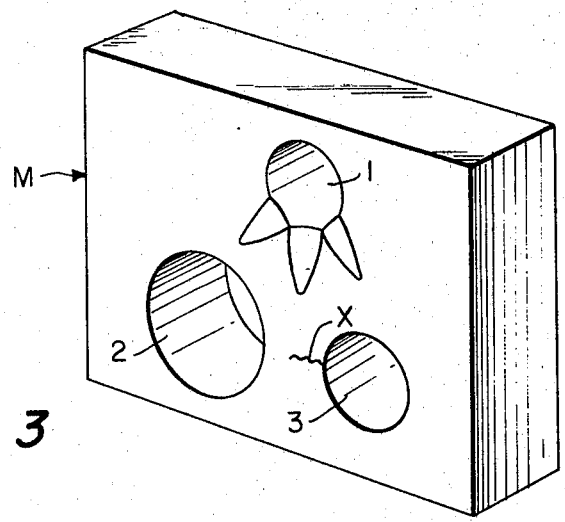
Figure 4:
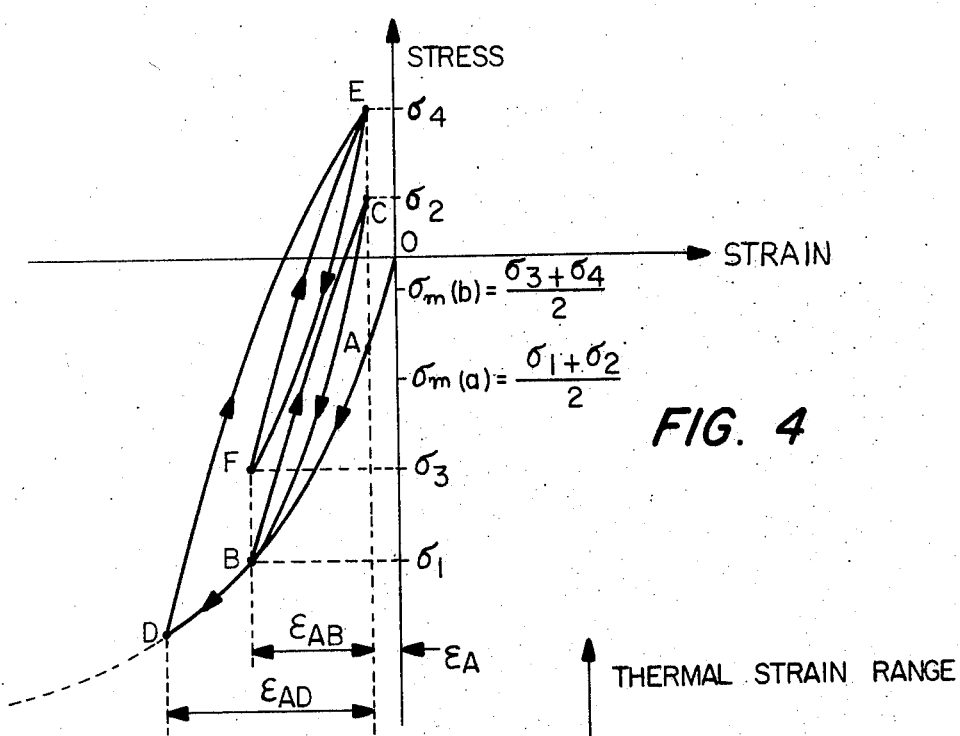
Figure 5:
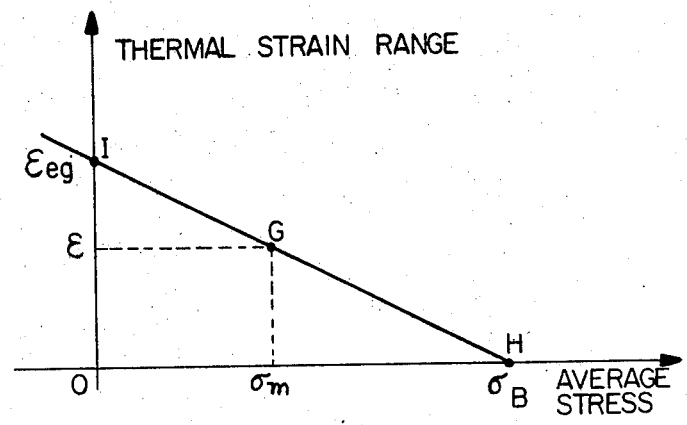
Figure 6:
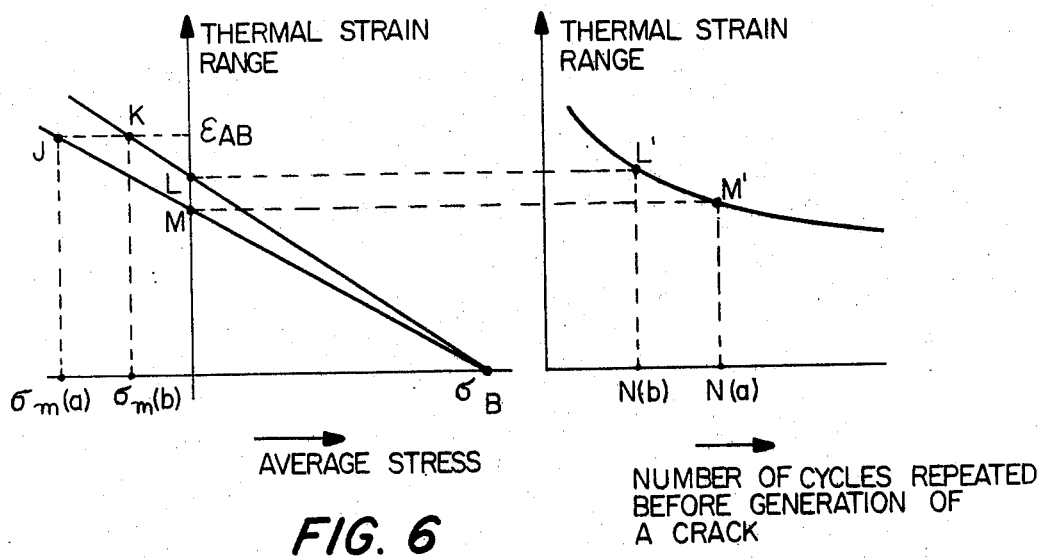

Above-mentioned and other features and objects of this invention will become more apparent by reference to the following description taken in conjunction with the accompanying drawings, in which:

FIG. 1 is a time chart showing the mode of endurance test in the prior art,

FIG. 2 is a time chart illustrating one preferred mode of endurance test according to the present invention, FIG. 3 is a schematic view of one model of test members to be used according to one preferred embodiment of the present invention, FIG. 4 is a stress-strain diagram to be used for comparatively explaining one preferred embodiment of the present invention in contrast to the prior art method, FIG. 5 is a Goodman's diagram showing the relation of thermal strains versus average stress, and FIG. 6 are diagrams for comparatively illustrating the method in the prior art and the method according to the present invention.

Explaining now one preferred embodiment of the method of endurance test according to the present invention with reference to the accompanying drawings, FIG. 2 shows the method of endurance test according to the present invention in contrast to the prior art method illustrated in FIG. 1, and the difference from the prior art method exists in the first cycle only, that is, the only difference exists in that only one first one of repeated loadings a predetermined overload is applied to a test member but upon second and subsequent loadings a load smaller than the first load is applied. Although this overloading is a dangerous operation as described above, if it is overloading for a very short period such as, for example, about 3 minutes, the danger would be small, and generally an overload as high as 130% is well applicable. In the second and subsequent cycles, an operation similar to that in the prior method is repeated.

By employing the above-described novel method it becomes possible to reduce an endurance test period (a number of repeated test cycles) until a thermal fatigue crack is generated in comparison to the prior art methods.

Now the principle of the present invention will be described.

FIG. 3 shows a position of a thermal fatigue crack that is typically generated in a cylinder head, and this figure is a model view of a cylinder head as viewed from the side of a combustion chamber (from the piston side). The description will be made in connection to the point indicating a typical position of occurrence of thermal fatigue (point X in the bridge portion between valves) in FIG. 3, but the same is also true in essence with respect to other locations where thermal fatigue cracks may arise. In FIG. 3, reference numeral 1 designates a pre-combustion chamber, numeral 2 designates an intake port, numeral 3 designates an exhaust port and character M designates a member to be tested.

FIG. 4 is a stress-strain diagram of a material from which a cylinder head is produced (materials of cast iron series being frequently used for a relatively small internal combustion engine having a cylinder diameter less than 200 - 300 mm). A curve O-B-D- shows a relation of stress versus strain when this material is compressed.

With reference to FIG. 4, description will be made on endurance test cycles (a) in the prior art (100% loading—stopping or idling as shown in FIG. 1). Point O represent the virgin state where the cylinder head has been manufactured and is subjected to no stress. The state where the cylinder head has been assembled in an engine and is subjected to an assembling stress is represented at point A. The strain in this state is represented by $\epsilon_A$. Here it is assumed that the stress condition at the point X shows the same stress value between the stopped state and the idling state of the engine.

Next, let us consider that the engine has been started and is operating at point B which corresponds to 100% loading. It is assumed that as a result of stress analysis it has been proved that the thermal strain corresponding to the thermal stress than acting upon point X of the cylinder head is $\epsilon_{AB}$. Then the stress actually generated in the material by plastic deformation is $\sigma_1$.

Now it is assumed that the loading for the engine has been reduced to point C in FIG. 1. Then the state of point C (See FIG. 4) is realized because a thermal strain component $\epsilon_{AB}$ corresponding to the variation of 100% loading—stopping or idling is recovered. The actual stress that is then caused by plastic deformation is represented by $\sigma_2$. Subsequently, as the test cycles of 100% loading—stopping or idling are applied to the test member, the state changes of C⇌B are repeated. An average stress $\sigma_m(a)$ in this case is determined by the equation written in FIG. 4.

Explaining now the endurance test (b) with initial overloading accordance to the present invention, the position of the state in FIG. 4 corresponding to the point A in FIG. 2 is the same as that in the prior art method. When an overloaded state is reached as shown by A→D in FIG. 2, in FIG. 4 the state comes to the position D through the path of A→B→D. The strain $\epsilon_{AD}$ at this moment can be obtained by stress analysis on the basis of the temperature distribution in the cylinder head when the engine is operating at the point D in FIG. 2.

Subsequently, when the load applied to the engine has been lowered down to the stop or idling state and it has come to the point E in FIG. 2, in FIG. 4 the state comes to the point E. Thereafter, if the test cycles of 100% loading—stopping or idling similar to the prior art method in FIG. 1 are repeated, then the state transition E~F will result in the same thermal strain change $\epsilon_{AB}$ as that in the prior art method, so that the state changes E⇌F as depicted in FIG. 4 are repeated. In this case the stress generated actually by plastic deformation is equal to $\sigma_4$ at the point E and $\sigma_3$ at the point F. Then the average stress $\sigma_m(b)$ is determined by the equation inscribed in FIG. 4.

It is to be noted that the shapes of the curves $\overline{OABD}$, B⇌C, D→E and E⇌F in the stress-strain diagram in FIG. 4 can be measured and defined through material tests for the cylinder head materials. In addition, the strains $\epsilon_A$, $\epsilon_{AB}$ and $\epsilon_{AD}$ can be obtained by stress analysis on the basis of temperature distribution in the cylinder head during operation of the engine under the respective load conditions. Therefore, the stresses $\sigma_1$, $\sigma_2$, $\sigma_3$, $\sigma_4$, $\sigma_m(a)$ and $\sigma_m(b)$ can be definitely determined in FIG. 4.

As described above, the difference between the method of endurance test in the prior art (a) and the endurance test with initial overloading according to the present invention (b) exists in that the average stresses $\sigma_m(a)$ and $\sigma_m(b)$ occurring at the point X in the cylinder head during the endurance test are different from each other.

It is known that in general the effects of the average stress upon a thermal fatigue strength can be obtained by means of a Goodman's diagram as illustrated in FIG. 5.

Now assuming that stress analysis at the point X during engine cycle operation has proved that the repeated traverse range of thermal strain is equal to $\epsilon$ and the average stress is equal to $\sigma_m$, this coordinate point ($\sigma_m$, $\epsilon$) is plotted in FIG. 5 as the point G. Next, a tensile strength $\sigma_B$ of the material is taken along the abscissa, and this point is marked H. Connecting the points G and H with a straight line, then the value of $\epsilon$ at the point I where the same straight line or its extension intersects with the ordinate is called an equivalent strain range $\epsilon_{eq}$.

The equivalent strain range $\epsilon_{eq}$ involves the following significance. That is, the number of cycles at which the material is destroyed by thermal fatigue when the repeated traverse range of thermal strain is $\epsilon$ and the average stress is $\sigma_m$, and the destructive number of cycles when the repeated traverse range of thermal strain is $\epsilon_{eq}$ and the average stress is 0, are equal to each other. It is known that such relation is also valid in the case of a negative average stress $\sigma_m$. While a thermal fatigue test at an average stress equal to 0 is practiced as a standard test generally in material tests, thermal fatigue lifes of existing practical machines and structures under various conditions acted thereupon can be inferred from the above-mentioned relation.

FIG. 6 gives comparative representatives of the respective characteristics of the endurance test in the prior art and the endurance test with initial overloading according to the present invention.

As will be apparent from the above discussion, the modes of repeated cycles of thermal strains generated during endurance tests are represented at point J in FIG. 6 in terms of an average strain $\sigma_m(a)$ in the prior art method, and at point K in terms of an average strain $\sigma_m(b)$ in the method according to the present invention. And, the respective equivalent traverse ranges of strain are derived at points M and L, respectively.

On the other hand, if the relation between the traverse range of thermal strain and the number of cycles repeated before generation of a crack is preliminarily obtained by thermal fatigue tests (under an average stress of 0) of materials as illustrated on the right side in FIG. 6, then the cracked generating numbers of repeated cycles N(a) (in the prior art) and N(b) (according to the present invention) can be obtained at points L' and M' in the same diagram. More particularly, N(b)<N(a) is satisfied, which means that the period of endurance test (the number of repeated cycles N) can be reduced according to the present invention. Furthermore, the period for endurance test (the number of repeated cycles N) to be conducted can be quantitatively and definitely inferred depending upon the magnitude of the loads to be applied in the endurance test with initial overloading.

Now describing the present invention in connection to examples of practical applications, the subject engine for test was an engine of the class of 60PS × 3300 rpm and cylinder diameter of 90 mm, whose cylinder head material was cast iron, and as the initial overloading 120% loading was applied. The following table shows the results of these tests:

| Method of Endurance Test | Temperature difference between a fire contact surface and a cooling surface at point X of a head | | Thermal Strain (%) | Number of Cycles Upon Occurrence of A Crack |
| --- | --- | --- | --- | --- |
| | Upon Maximum Loading | Upon Idling | | |
| Prior Art Test | | | | |

-continued

| Method of Endurance Test | Temperature difference between a fire contact surface and a cooling surface at point X of a head | | Thermal Strain (%) | Number of Cycles Upon Occurrence of A Crack |
|---|---|---|---|---|
| | Upon Maximum Loading | Upon Idling | | |
| Method (a) | 254° C | 33° C | $\epsilon_{AB}=0.400$ | 4600 |
| Method of Endurance Test With Initial Overloading According To The Present Invention (b) | 334° C (Initial Overloading) | 33° C (Similar to the left) | $\epsilon_{AP}=0.570$ (Similar to the left) | 1500 |
| | 254° C (Second & Subsequent Cycles) | 33° C (Similar to the left) | $\epsilon_{AB}=0.400$ (Similar to the left) | |

As a result, in comparison to the method of endurance test in the prior art, according to the present invention generation of a crack can be confirmed at a number of repeated cycles about ⅓ times as small as that in the prior art method. Accordingly, the method of endurance test with initial overloading according to the present invention can be completed within a test period about ⅓ times as short as that in the prior method, that is within a period of 3 weeks to 1 month.

In addition, since the method of the present invention is a quantitatively defined method as described above, it can properly estimate an endurance of an engine operating practically in the market.

Still further, with regard to the danger that may accompany the endurance test, there is an additional merit that the degree of danger can be reduced in comparison to the case where over-load operations are repeated according to the prior art method, because according to the present invention an overload operation is conducted only for a very short period of time.

Thus, according to the method of endurance test of the present invention, the test period and cost required upon development of a new type engine and upon change of design, can be widely reduced.

While the principles of the present invention have been described above in connection with specific member to be tested, it is to be clearly understood that this description is made only by way of example and not as a limitation to the scope of the invention as set forth in the accompanying claims.

What is claimed is:

1. A method of endurance test with initial overloading in which a load is repeatedly applied to a test member, characterized in that upon first one of said repeated loadings an overload is applied but upon second and subsequent loadings a load smaller than the first load is applied.

* * * * *